(12) United States Patent
Forbes Jones et al.

(10) Patent No.: US 8,048,369 B2
(45) Date of Patent: Nov. 1, 2011

(54) COBALT-NICKEL-CHROMIUM-MOLYBDENUM ALLOYS WITH REDUCED LEVEL OF TITANIUM NITRIDE INCLUSIONS

(75) Inventors: Robin M. Forbes Jones, Charlotte, NC (US); Henry E. Lippard, Monroe, NC (US); Timothy A. Stephenson, Waxhaw, NC (US); Robert J. Myers, Fort Wayne, IN (US); David J. Bradley, Fort Wayne, IN (US)

(73) Assignee: ATI Properties, Inc., Albany, OR (US)

( * ) Notice: Subject to any disclaimer, the term of this patent is extended or adjusted under 35 U.S.C. 154(b) by 964 days.

(21) Appl. No.: 10/656,918

(22) Filed: Sep. 5, 2003

(65) Prior Publication Data

US 2005/0051243 A1    Mar. 10, 2005

(51) Int. Cl.
*C22C 30/00*    (2006.01)
(52) U.S. Cl. ...................................... 420/588; 148/442
(58) Field of Classification Search .................. 420/588; 148/442
See application file for complete search history.

(56) References Cited

U.S. PATENT DOCUMENTS

| | | | |
|---|---|---|---|
| 2,103,500 A | | 12/1937 | Touceda |
| 3,241,954 A | * | 3/1966 | Thielemann ................. 420/436 |
| 3,356,542 A | | 12/1967 | Smith |
| 3,562,024 A | | 2/1971 | Smith |
| 3,787,202 A | * | 1/1974 | Mueller et al. ............... 420/428 |
| 3,816,106 A | * | 6/1974 | Snape ........................... 420/585 |
| 4,099,992 A | | 7/1978 | Pugliese et al. |
| 4,151,012 A | | 4/1979 | Simkovich et al. |
| 4,353,742 A | * | 10/1982 | Crook ........................... 420/585 |
| 4,355,646 A | | 10/1982 | Kallok et al. |
| 4,474,733 A | * | 10/1984 | Susukida et al. ............. 420/443 |
| 4,591,393 A | | 5/1986 | Kane et al. |
| 4,820,485 A | * | 4/1989 | Ototani et al. ................. 420/78 |
| 5,246,014 A | | 9/1993 | Williams et al. |
| 5,411,545 A | | 5/1995 | Breyen et al. |
| 5,423,881 A | | 6/1995 | Breyen et al. |
| 5,433,744 A | | 7/1995 | Breyen et al. |
| 5,483,022 A | | 1/1996 | Mar |
| 5,637,159 A | | 6/1997 | Erickson |
| 5,692,899 A | | 12/1997 | Takahashi et al. |
| 5,760,341 A | | 6/1998 | Laske et al. |
| 6,061,598 A | | 5/2000 | Vemess et al. |
| 6,187,045 B1 | | 2/2001 | Fehring et al. |
| 6,248,955 B1 | | 6/2001 | Avellanet |
| 6,342,068 B1 | * | 1/2002 | Thompson .................. 623/1.53 |
| 6,539,607 B1 | | 4/2003 | Fehring et al. |
| 6,720,497 B1 | | 4/2004 | Barsne |
| 7,015,392 B1 | | 3/2006 | Dickenson |
| 2002/0033717 A1 | | 3/2002 | Matsuo |
| 2002/0068965 A1 | * | 6/2002 | Sass ............................ 607/122 |
| 2002/0147488 A1 | | 10/2002 | Doan et al. |
| 2004/0267107 A1 | | 12/2004 | Lessar et al. |
| 2005/0004643 A1 | | 1/2005 | Ebert et al. |
| 2005/1002734 | | 2/2005 | Shoberg at al. |

FOREIGN PATENT DOCUMENTS

| | | |
|---|---|---|
| JP | 10-140279 A | 5/1998 |
| JP | 2003-49249 A | 2/2003 |

OTHER PUBLICATIONS

Bradley, et al., "Optimization of Melt Chemistry and Properties of 35Cobalt-35Nickel-20Chromium-10 Molybdenum Alloy Medical Grade Wire", submitted to ASM International on Sep. 5, 2003.
Cockcroft, S. et al., "Inclusions and the EB Refining of Superalloys," Proceedings of the Conference, Electron Beam Melting and Refining State of the Art 1992, John K. Tien Memorial Conference, p. 143-159 (1992).
Koenig, R., "The Federal Aviation Administration's (FAA's) Approach to Turbine Engine Certification as it Applies to Critical Titanium Components, "Proceedings of the Conference, Electron Beam Melting and Refining State of the Art 1991, p. 27-30 (1991).
ASTM F 1058-02 Standard Specification for Wrought 40Cobalt-20Chromium-16Iron-15Nickel-7Molybdenum Alloy Wire and Strip for Surgical Implant Applications (UNS R30003 and UNS R30008), ASTM International (Apr. 10, 2002).
ASTM F 562-02 Standard Specification for Wrought 35Cobalt-35Nickel-20Chromium-10Molybdenum Alloy for Surgical Implant Applications (UNS R30035), ASTM International (Apr. 10, 2002).
International Search Report and Written Opinion of the International Searching Authority mailed Oct. 8, 2004, corresponding PCT application No. PCT/US2004/15628.
Declaration of Robert J. Myers, dated Nov. 7, 2005.
Declaration Exhibit 1—Purchase Order 18479 dated May 2, 1994.
Declaration Exhibit 2—Receiving Inspection Report dated Mar. 20, 1995.
Declaration Exhibit 3—Certificate of Tests dated Mar. 13, 1995.
Declaration Exhibit 4—Invoice Record of Invoice 53776 dated Aug. 14, 1995.
Declaration Exhibit 5—Purchase Order 100410 dated Dec. 11, 2002.
Declaration Exhibit 6—Certificate of Tests dated Dec. 10, 2002.
Declaration Exhibit 7—Correspondence dated Aug. 13, 1998.
Declaration Exhibit 8—Laboratory Report dated Jul. 16, 2003.

* cited by examiner

*Primary Examiner* — Jessee R. Roe
(74) *Attorney, Agent, or Firm* — K & L Gates LLP; Patrick J. Viccaro; John E. Grosselin, III

(57) ABSTRACT

A cobalt-nickel-chromium-molybdenum alloy useful in surgical implant applications includes, in weight percent based on total alloy weight, at least 20 cobalt, 33.0 to 37.0 nickel, 19.0 to 21.0 chromium, 9.0 to 10.5 molybdenum, and less than 30 ppm nitrogen. Embodiments of the alloy lack significant levels of titanium nitride and mixed carbonitride inclusions. The alloy may be cold drawn to thin-gauge wire without damage to the die as may be caused by hard particle inclusions in certain conventional alloy formulations.

22 Claims, 12 Drawing Sheets

Heat WF64 - LLA Mg Deoxidation

| Size | Composition | |
|---|---|---|
| 0.5 µm | Mg | oxide |
| 0.5 x 1.2 µm | Mg | oxide |
| 0.8 µm | Mg | oxide |
| 0.6 µm | Mg | oxide |
| 11 x 0.8 µm | Mg | oxide |
| 12 x 0.8 µm | Mg/Al | oxide |
| 1 µm | Mg | oxide |
| 1.6 µm | Mg | oxide |
| 1.2 µm | Mg | oxide |
| 1.6 µm | Mg | oxide |
| 0.8 µm | Al | oxide |
| 1 µm | Mg | oxide |
| 9 x 0.6 µm | Al/Si | oxide |

ASTM E45 - Method D (worst Field)
Globular Type D Thin = 0.5
All others = 0

Grain Size - ASTM 10

Heat WF66 - LLA Ce Deoxidation

| Size | Composition | |
|---|---|---|
| 2.4 x 0.9 µm | Ce | oxide |
| 2.2 µm | Ce | oxide |
| 1 µm | Ce | oxide |
| 1 µm | Ce | oxide |
| 1 µm | Ce | oxide |
| 1.5 µm | Ce | oxide |
| 4 x 2 µm | Ce | oxide |
| 1.6 µm | Ce | oxide |
| 3.2 µm | Ce | oxide |
| 15 x 2 µm | Ce | oxide |
| 0.7 µm | Ce | oxide |
| 5.4 x 2.4 µm | Ce | oxide |
| 4.3 x 0.4 µm | Ce | oxide |

ASTM E45 - Method D (worst Field)
Globular Type D Thin = 1.0
All others = 0

Grain Size - ASTM 10

Heat WF65 - LLA Ca Deoxidation

| Size | Composition | |
|---|---|---|
| 0.8 µm | Al | oxide |
| 0.8 µm | Al | oxide |
| 1.8 µm | Al | oxide |
| 2 µm | Al | oxide |
| 1.7 µm | Al | oxide |
| 1.5 µm | Al | oxide |
| 2 µm | Al | oxide |
| 1.2 µm | Al | oxide |
| 1 µm | Ca | oxide |
| 1.2 µm | Al | oxide |
| 12 x 1 µm | Al/Ca | oxide |
| 90 µm | | |
| stringer = total length of 90 µm | | |

ASTM E45 - Method D (worst Field)
Globular Type D Thin = 0.5
Sulfide Type A Thin = 0.5
All others = 0

Grain Size - ASTM 10

Figure 20

COBALT-NICKEL-CHROMIUM-MOLYBDENUM ALLOYS WITH REDUCED LEVEL OF TITANIUM NITRIDE INCLUSIONS

BACKGROUND OF THE INVENTION

Field Of The Invention

The present disclosure is directed to alloys including cobalt, nickel, chromium and molybdenum, wherein the alloys exhibit favorable fatigue strength and may be processed to bar, wire and other forms without exhibiting an unacceptable tendency to develop surface defects or to fracture or crack during cold drawing or forging. The present disclosure also is directed to methods of making the alloys described in the present disclosure, and to articles of manufacture made from or including such alloys. Such articles of manufacture include, for example, bar and wire, including small-diameter wire intended for use in stents, pacing leads for implantable defibrillators or pacemakers, and other surgical implant applications.

DESCRIPTION OF THE INVENTION BACKGROUND

Specialized alloys have been developed for surgical implant applications. One such alloy, known as "MP35N" alloy (UNS R30035), is produced in bar and wire forms intended for use in surgical implants such as, for example, cardiac stents and pacing leads adapted to relay a pacing pulse from an implanted defibrillator or pacemaker to the heart. An example of a pacing lead is shown in FIG. 1. Standard specifications for wrought MP35N alloy for use in surgical implant applications may be found in ASTM specification F 562-02, the entire disclosure of which is hereby incorporated herein by reference. As provided in the ASTM specification, MP35N alloy to be used in surgical implant applications must have the chemistry provided in Table 1 below. In order to account for acceptable variation between laboratories in the measurement of chemical content, however, the ASTM specification (Table 2 of ASTM F 562-02) permits the measured chemistry of MP35 alloy to vary from the minimum or maximum values shown in Table 1 by the amounts shown in the rightmost column in Table 1. As used in the present disclosure, "MP35N" alloy refers to a cobalt-nickel-chromium-molybdenum alloy having a chemical composition as described in Table 1 below and in ASTM specification F 562-02.

TABLE 1

| Element | Composition, % (mass/mass) Min. | Composition, % (mass/mass) Max. | Tolerance Under the Min. or Over the Max. Limit % (mass/mass)* |
|---|---|---|---|
| Carbon | — | 0.025 | 0.01 |
| Manganese | — | 0.15 | 0.03 |
| Silicon | — | 0.15 | 0.02 |
| Phosphorus | — | 0.015 | 0.005 |
| Sulfur | — | 0.010 | 0.005 |
| Chromium | 19.0 | 21.0 | 0.25 |
| Nickel | 33.0 | 37.0 | 0.30 |
| Molybdenum | 9.0 | 10.5 | 0.15 |
| Iron | — | 1.0 | 0.05 |
| Titanium | — | 1.0 | 0.04 |
| Boron | — | 0.015 | 0.005 |
| Cobalt | balance | balance | — |

*Under minimum limit not applicable for elements where only a maximum percentage is indicated.

Certain technical problems may be encountered during the manufacture of MP35N alloy for use in pacing leads and other surgical implant applications. In particular, problematic surface defects may appear when cold drawing the alloy to wire. When drawing the alloy to small-gauge wire for use as pacing leads, for example, surface defects are most likely to develop during the late stages of the drawing process, when the wire approaches the 0.007 inch diameter final size typically used for such applications. Drawing-related surface defects are particularly problematic because they may appear after significant time and money is invested in the product. As the wire approaches a small diameter, the surface defects may cause the wire to fracture during cold drawing. This results in lower process yields during wire production, which can significantly increase the cost of the wire. Pacing leads and other surgical implants formed from MP35N alloy wire having surface defects also may have reduced fatigue resistance and may be susceptible to fracture. The resultant reduced service life may require premature replacement of the implant.

Given the foregoing technical problems encountered during cold drawing of conventional MP35N alloy, there is a need for a cobalt-nickel-chromium alloy suitable for similar surgical implant applications and that also exhibits improved fatigue strength and may be suitably processed to bar, wire and other suitable forms without an unacceptable tendency to develop surface defects or to fracture or crack during cold drawing or forging.

SUMMARY

In order to address the foregoing needs, the present disclosure is directed to an alloy including, in weight percent based on total alloy weight: at least 20 cobalt; 32.7 to 37.3 nickel; 18.75 to 21.25 chromium; 8.85 to 10.65 molybdenum; and less than 30 ppm nitrogen. In certain embodiments, the alloy is wholly or substantially free of titanium nitride and mixed metal carbonitride inclusions.

The present disclosure is further directed to an alloy including, in weight percent based on total alloy weight: at least 20 cobalt; 33.0 to 37.0 nickel; 19.0 to 21.0 chromium; 9.0 to 10.5 molybdenum; no greater than 0.025 carbon; no greater than 0.15 manganese; no greater than 0.15 silicon; no greater than 0.015 phosphorus; no greater than 1.0 titanium; no greater than 0.010 sulfur; no greater than 1.0 iron; and no greater than 0.015 boron. The alloy is wholly or substantially free of titanium nitride and mixed metal carbonitride inclusions.

The present disclosure is further directed to articles of manufacture including any of the novel alloys described herein. Examples of article of manufacture include a bar, a wire, a tube, a surgical implant device, a component for a surgical implant device, an implantable defibrillator, a component for an implantable defibrillator, an implantable pacemaker, a component for an implantable pacemaker, a pacing lead, and a cardiac stent. In instances where the article of manufacture is a bar or a wire, the article also may be one qualified for use in surgical implant applications under ASTM standard specification F 562.

The present disclosure is additionally directed to a method of making an alloy, wherein the method includes preparing a VAR ingot having a composition including, in weight percent based on total alloy weight: at least 20 weight percent cobalt; 33.0 to 37.0 weight percent nickel; 19.0 to 21.0 weight percent chromium; 9.0 to 10.5 weight percent molybdenum; and less than 30 ppm nitrogen. In certain embodiments of the method, the ingot is wholly or substantially free of titanium nitride and mixed metal carbonitride inclusions. The method may also include processing the ingot into one of a bar, a wire, and a tube, which may be further processed into one of a surgical implant device, a component for a surgical implant device, a component for an implantable defibrillator, a component for an implantable pacemaker, a pacing lead, and a cardiac stent.

The novel alloy of the present disclosure is a cobalt-nickel-chromium-molybdenum alloy that, in certain embodiments, exhibits significantly improved surface finish when drawn to wire relative to the surface finish commonly exhibited by drawn wire produced from MP35N alloy having a conventional chemistry. Embodiments of the alloy of the present disclosure also exhibit improved fatigue resistance relative to conventional MP35N alloy and benefit from a significantly lower fracture rate compared to conventional MP35N alloy when drawn to small diameter as required for use in pacing leads and certain other surgical implant applications.

These and other advantages will be apparent upon consideration of the following description of certain embodiments.

BRIEF DESCRIPTION OF THE FIGURES

Embodiments of the present invention will be understood by reference to the following figures, wherein:

FIG. 21 provides results of SEM analysis of experimental MP35N materials processed using various methods of deoxidation.

DESCRIPTION OF EMBODIMENTS

Figure 1:
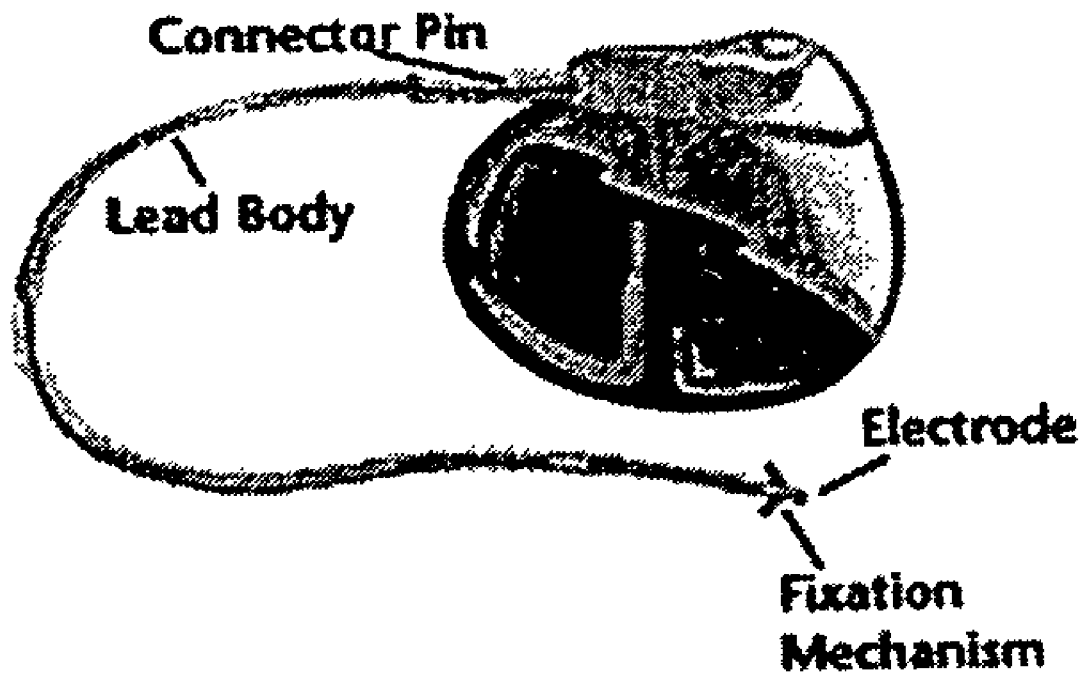
FIG. 1 is an illustration of an embodiment of a pacing lead.

It has been determined that the poor performance of MP35N alloy during cold drawing and forging to the presence of large, hard titanium nitride (TiN) inclusions. Also, in MP35N alloys including relatively high nitrogen levels, large, hard cuboidal mixed metal carbonitride inclusions may form in the alloys. The mixed metal carbonitrides are principally titanium and chromium carbonitrides. The principal failure mechanism of the conventional MP35N alloy upon drawing and forging is fatigue initiation at the particulate inclusions. The TiN and mixed metal carbonitride inclusions may form during solidification of the alloy after melting, and the particles cannot be removed or broken up by subsequent heat treatment or thermomechanical processing. Instead, it has been determined that the inclusions are retained in their as-cast size in the final product.

The hard TiN and mixed metal carbonitride particles damage the drawing die during cold drawing of conventional MP35N material. Wire drawn through a damaged die may have surface defects in the form of scratches on the wire surface. Die damage and resulting wire surface defects significantly reduce yield. As the drawn wire becomes smaller in diameter, the nitride and carbonitride particles take up a larger portion of the wire cross-section and, therefore, weaken the material, thus creating fractures during drawing. The particles also act as stress raisers during fatigue loading and contribute to the initiation of fatigue cracks, which can result in the premature failure of the material and the associated device.

Embodiments of the cobalt-nickel-chromium-molybdenum alloy of the present disclosure have chemistries within the ranges listed above in Table 1 and in ASTM specification F 562. The embodiments, however, have a chemistry that differs from the conventional chemistry of MP35N alloy. These chemistry differences provide an alloy that, although falling within the broad chemistry for MP35N alloy included in ASTM specification F 562, includes levels of nitrogen and/or titanium that are substantially lower than in conventional MP35N alloy. For example, conventional MP35N alloy produced under ASTM specification F 562 typically includes at least about 50 ppm nitrogen and about 0.95 weight percent titanium. The differences in chemistry in the modified MP35N alloys to which the present disclosure is directed have been found to inhibit the formation of hard TiN and mixed metal carbonitride particulate inclusions in the alloys. This, in turn, improves the ability to process the alloy to bar and wire form and enhances the fatigue resistance of alloy and products produced from the alloy.

Accordingly, embodiments of the cobalt-nickel-chromium-molybdenum alloy of the present disclosure do not include significant levels of TiN and mixed metal carbonitride particulate inclusion, and the alloys may be free or substantially free of such particles. The absence of significant levels of the hard particles inhibits damage to drawing dies, and thereby significantly improves the surface finish of drawn wire relative to conventional MP35N alloy drawn through damaged dies. The reduction in levels of TiN and mixed metal carbonitride particles also significantly improves fatigue resistance of the modified MP35N alloys described herein relative to wire and other articles formed from conventional MP35N alloys using conventional processing. Also, because significant levels of TiN and mixed metal carbonitride particles are absent, a lower incidence of wire breakage is experienced wire drawing.

Accordingly, the forgoing improvements in performance and character of the modified MP35N alloys described herein are obtained by significantly reducing or eliminating the presence of certain particulate inclusions in the alloys. This may be accomplished, for example, by reducing the level of nitrogen and/or titanium in the raw materials used to produce the melt charge. Reduction in nitrogen and/or titanium may also be accomplished by suitably processing the materials prior to cold working or forging the materials. Those having ordinary skill in the art, upon reading the present disclosure, may comprehend additional methods for reducing nitrogen and/or titanium levels in MP35N alloys, and it is intended that all such methods, although not expressly mentioned herein, are encompassed by the present disclosure.

Embodiments of the cobalt-nickel-chromium-molybdenum alloys of the present disclosure also may be formulated or processed to limit oxygen to levels that are significantly lower than in conventional MP35N alloys. Such reduction aids in the ability to hot work the modified MP35N alloys of the present disclosure without fracturing the material. In order to better ensure that the alloys of the present disclosure do not crack during forging to bar or wire, for example, steps may be taken to inhibit the occurrence of oxygen embrittlement at grain boundaries in the alloy. This may be accomplished by, for example, certain deoxidation techniques described in the examples below.

Figure 2:
FIG. 2 is a photomicrograph of a typical TiN precipitate, including an aluminum oxide core, found in conventional MP35N alloy.
Figure 3:
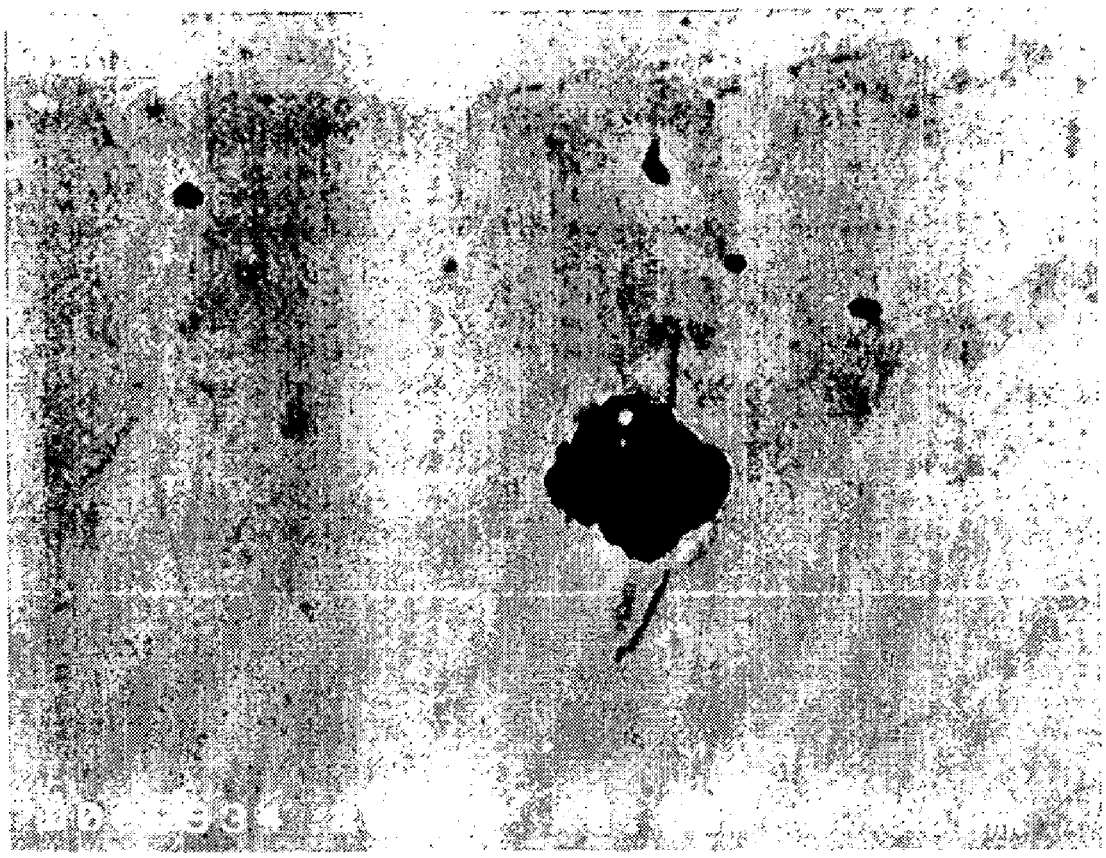
FIG. 3 is a photomicrograph of a typical aluminum oxide particle found in conventional MP35N alloy.

The standard production melting route for conventional MP35N alloy for use in pacing leads and other surgical implant applications under ASTM specification F 562 is a combination of vacuum induction melting (VIM) and vacuum arc remelting (VAR). Typical ladle and ingot chemistries of conventional MP35N alloy are provided in Table 2 below (levels of nitrogen and certain other elements were not determined). The average particle size observed in the conventional MP35N material was a cuboidal 6 micrometer TiN precipitate with a 1-2 micrometer spherical $Al_2O_3$ core, and one such particle is shown in FIG. 2. Aluminum oxides without a TiN shell also were observed in the conventional material, as shown in FIG. 3. In order to significantly reduce or eliminate occurrence of TiN and mixed metal carbonitride particles in the microstructure of the alloys of the present disclosure, one route is to judiciously select higher quality raw materials including suitably reduced levels of nitrogen and/or titanium. Although the reduction in nitrogen levels in the alloy will inhibits the formation of TiN and mixed metal carbonitrides, the solubility of nitrogen in MP35N alloy is unknown, so elimination of nitride formers such as titanium in the present melt practice for MP35N alloy also was considered. Reduction or elimination of titanium, for example, was considered possible in applications such as, for example, pacing leads, which are not strength limited and because the ASTM specification for such applications does not include a minimum strength limit.

Experimental results describing a limited number of embodiments of modified MP35N alloys within the present disclosure follow.

EXAMPLE 1

Four 150 lb. heats, designated WE48, WE52, WE53 and WE54, were VIM-VAR processed and forged to 5-inch RD billets. The ladle chemistry of each heat is provided in Table 2, along with ladle and VIM chemistries for certain heats of conventional MP35N alloy. The experimental modified MP35N heats were formulated with the general aims for titanium and nitrogen indicated in Table 3 relative to the typical chemistry for conventional MP35N alloy produced under ASTM specification F 562. For purposes of Table 3 only, "high" titanium was considered 0.70 weight percent or greater, and "low" titanium was considered concentrations in the ppm range. Also for purposes of Table 3 only, "high" nitrogen was considered 0.01 weight percent or greater, and "low" nitrogen was considered less than 0.001 weight percent. It is to be understood that the use of the terms "high" and "low" in connection with Table 3 as just described has no relationship or bearing on the meaning of such terms as may be used elsewhere in the present disclosure or in the accompanying claims.

One experimental heat, WE48, experienced severe cracking during forging and was unsuitable for rolling. The remaining heats were rolled on hand mills to 1.047-inch RD bars. The heats were evaluated for microcleanliness and mechanical properties after annealing the bars.

TABLE 2

|  | Conventional MP35N Alloy VIM Ladle (n = 21) | | Conventional MP35N Alloy ESR Ingot Average (n = 29) | | Experimental Heats VIM Ladle | | | |
|---|---|---|---|---|---|---|---|---|
|  | Average | SD | Top | Bottom | WE52 | WE54 | WE53 | WE48 |
| Ni | 36.11 | 0.37 | 36.16 | 36.32 | 36.18 | 36.20 | 36.22 | 36.40 |
| Co | 32.47 | 0.59 | 32.59 | 32.26 | 32.81 | 32.69 | 33.32 | 33.41 |
| Cr | 19.98 | 0.27 | 20.02 | 20.00 | 19.82 | 19.86 | 19.89 | 19.57 |
| Mo | 10.01 | 0.11 | 10.01 | 10.01 | 10.09 | 10.12 | 10.11 | 10.15 |
| Ti | 0.95 | 0.03 | 0.71 | 0.76 | 0.77 | 0.80 | ppm | ppm |
| Fe | 0.30 | 0.22 | 0.35 | 0.41 | 0.23 | 0.22 | 0.23 | 0.23 |
| Al | 0.05 | 0.035 | 0.01 | 0.07 | 0.01 | 0.01 | 0.01 | 0.01 |
| Mn | 0.03 | 0.027 | 0.03 | 0.04 | 0.01 | 0.02 | 0.01 | 0.01 |
| Zr | 0.02 | 0.000 | 0.02 | 0.02 | 0.02 | 0.02 | 0.02 | 0.02 |
| W | 0.01 | 0.010 | 0.02 | 0.02 | 0.01 | 0.01 | 0.01 | 0.01 |
| Si | 0.01 | 0.009 | 0.01 | 0.02 | 0.01 | 0.01 | 0.02 | 0.04 |

TABLE 2-continued

|   | Conventional MP35N Alloy VIM Ladle (n = 21) | | Conventional MP35N Alloy ESR Ingot Average (n = 29) | | Experimental Heats VIM Ladle | | | |
|---|---|---|---|---|---|---|---|---|
|   | Average | SD | Top | Bottom | WE52 | WE54 | WE53 | WE48 |
| Nb | 0.01 | 0.004 | 0.01 | 0.04 | 0.01 | 0.01 | 0.01 | 0.01 |
| Cu | 0.01 | 0.000 | 0.01 | 0.01 | 0.01 | 0.01 | 0.01 | 0.01 |
| Ta | 0.01 | 0.000 | 0.01 | 0.01 | 0.01 | 0.01 | 0.01 | 0.01 |
| V | 0.01 | 0.000 | 0.01 | 0.02 | 0.01 | 0.01 | 0.01 | 0.01 |
| B | 0.0074 | 0.0006 | 0.0074 | 0.0050 | 0.008 | 0.012 | 0.006 | 0.005 |
| C | 0.004 | 0.003 | 0.005 | 0.007 | 0.002 | 0.004 | 0.005 | 0.006 |
| S | 0.0010 | 0.0006 | 0.0012 | 0.0006 | 0.0008 | 0.0007 | 0.0007 | 0.0014 |
| P |   |   |   |   | <.003 | <.003 | <.003 | <.003 |
| N |   |   |   |   | 0.0006 | 0.0058 | 0.0194 | 0.0006 |
| O |   |   |   |   | 0.0009 | 0.0012 | 0.0016 | 0.0051 |

TABLE 3

| Heat | Titanium | Nitrogen |
|---|---|---|
| WE48 | Low | Low |
| WE52 | High | Low |
| WE53 | Low | High |
| WE54 | High | High |

Mechanical properties and grain sizes of bar produced from heats WE52, WE53 and WE54 are provided in Table 4. The bar was annealed at 1925° F. for 2 hours, and then water quenched before testing.

TABLE 4

| Heat | UTS (ksi) | 0.2% YS (ksi) | Elong. (%) | RA (%) | Grain Size (ASTM) |
|---|---|---|---|---|---|
| WE52 | 131.2 | 50.5 | 70.0 | 81.0 | 5 |
| WE53 | 133.2 | 52.3 | 68.3 | 81.5 | 6.5 |
| WE54 | 135.4 | 54.4 | 65.3 | 78.4 | 6.5 |

Figure 4:
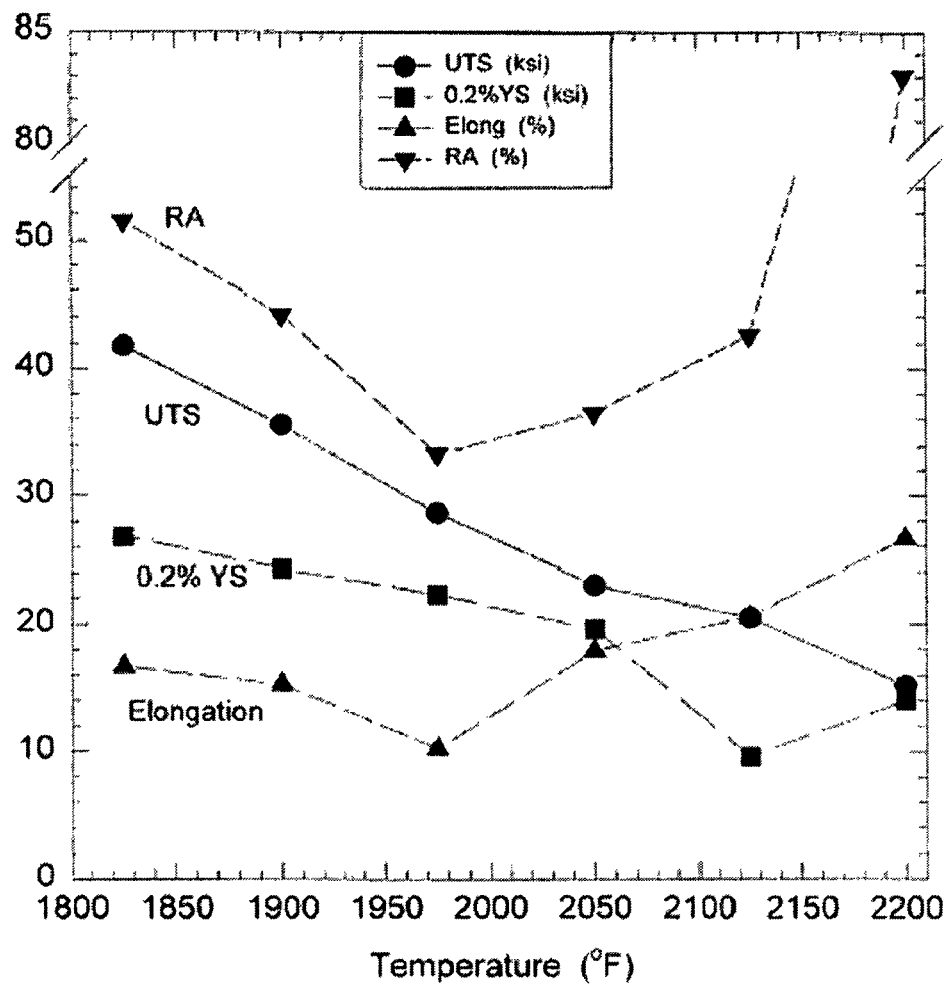
FIG. 4 is a graph showing results of rapid strain rate hot tensile testing of experimental heat WE48 in Example 1 herein.

Rapid strain rate hot tensile testing was used to measure the ductility of heat WE48 that had cracked severely during press forging. The results are shown in FIG. 4. The low ductility of the material was attributed to the high oxygen level, 51 ppm, and the lack of oxide formers such as aluminum and titanium, which would form compounds to prevent oxygen embrittlement of grain boundaries. The other low titanium heat, WE53, which had an oxygen level of 16 ppm, did not experience forge or roll cracking. This result indicated that the oxygen levels in the low titanium heats were near an intermediate unstable boundary that can be easily influenced by small processing and/or chemistry variations. Accordingly, additional heats were considered with a processing regimen including a more robust deoxidation practice to prevent significant occurrence of oxygen embrittlement at the grain boundaries.

Figure 5:
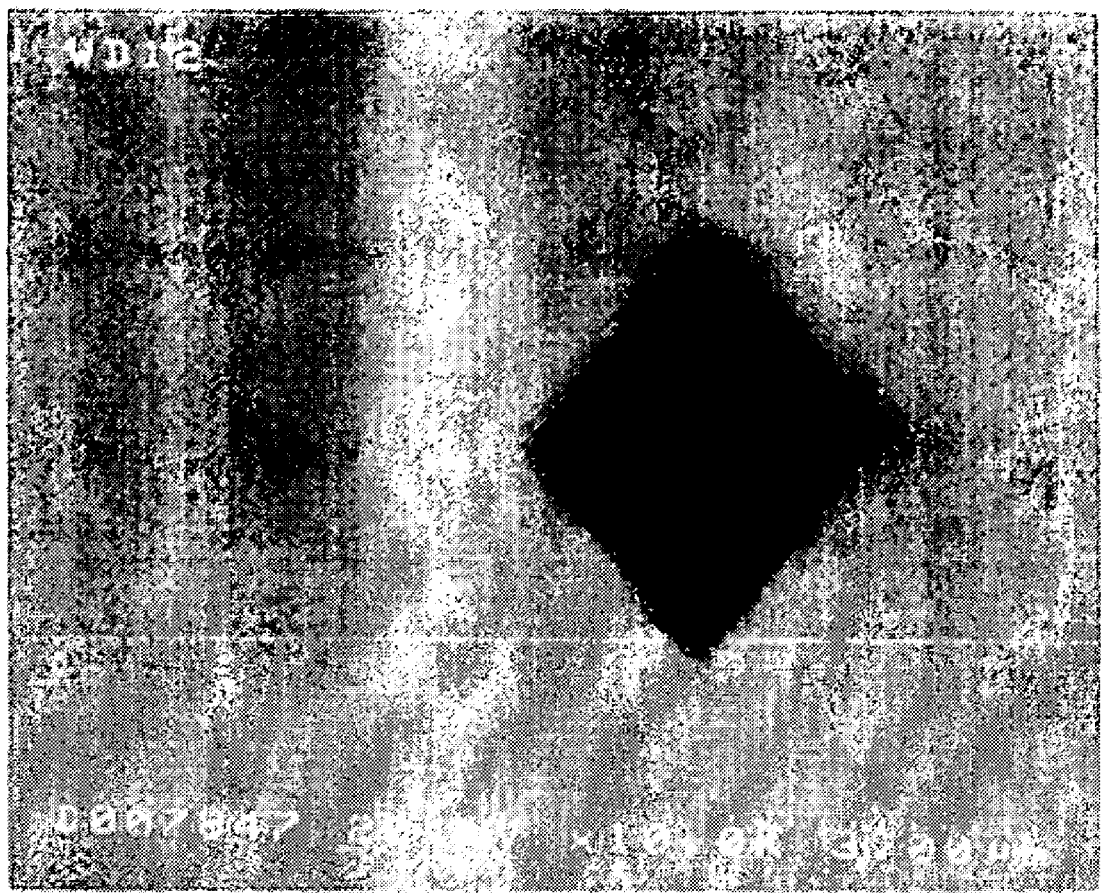
FIG. 5 is an SEM image of a titanium nitride particle (approximately 3 micrometers in diameter) in high-titanium, high-nitrogen experimental heat WE54 of Example 1 herein.

Microcleanliness evaluations of heat WE48, which included the lowest levels of both titanium and nitrogen, and heat WE54, which included the highest levels of both titanium and nitrogen, were conducted by standard ASTM E45 and random particle analysis on the scanning electron microscope (SEM). The ASTM E45 measurements at 100× did not detect any particles. The SEM analysis of WE54 revealed TiN particles of approximately 3 micrometers in size. One such particle is shown in FIG. 5. The particle size was somewhat smaller than typical TiN particles in conventional MP35N alloy produced in production heats. It is believed that the slight reduction in TiN particle size in heat WE54 relative to production heats of conventional MP35N alloy was a function of the faster cooling rate of the smaller pilot plant VAR process used in the production of the experimental heats relative to the production-scale VAR process. No particles were detected by SEM analysis in heat WE48 (with respect to Table 3, the low titanium, low nitrogen heat).

Based on the results in this example, one preferred embodiment of the modified MP35N alloy includes no more than ppm levels of nitrogen, and may also include levels of titanium that are lower than in conventional MP35N material. Based on the results, one preferred embodiment of modified MP35N alloy includes less than 30 ppm of nitrogen to inhibit any significant formation of TiN and mixed metal carbonitride. A more preferred level is less than 20 ppm nitrogen, which would better ensure that the problematic particulate inclusions are not present in the material. Such levels of nitrogen are significantly lower than in conventional MP35N material formulated to ASTM specification F 562. In addition, the alloy of the present disclosure optionally may include less than 0.7 weight percent titanium, and more preferably less than 0.03 weight percent titanium, in order to better ensure the absence of any significant levels of TiN and mixed metal carbonitride particles.

It also is preferred that the modified MP35N alloys of the present disclosure include a sufficient level of deoxidization so as to inhibit grain boundary oxygen embrittlement and allow suitable hot workability. This may be accomplished, for example, by including 0.05 to 0.15 weight percent aluminum in the alloy to sufficiently reduce the oxygen level in the processed alloy. It is expected that the aluminum would promote formation of small (i.e., less than 3 micrometer), generally spherical aluminum oxide particles that are significantly less detrimental to fatigue life properties than the cuboidal TiN particles typically present in conventional MP35N. Other techniques for reducing the oxygen content of the alloy are discussed in the examples below and include modifying the deoxidation practice during VIM melting of the charge.

A reliable method for wholly or substantially eliminating TiN and mixed metal carbonitride inclusions is by wholly or substantially eliminating one or both of nitrogen and titanium from the charged raw materials. Wholly or substantially eliminating both nitrogen and titanium from the raw materials is preferred inasmuch as doing so provides a margin of safety if significant levels of either element are inadvertently introduced into the charge. However, it was determined that eliminating all or substantially all of the titanium from the MP35N alloy results in only marginal deoxidation of the alloy during processing and produces an alloy having relatively low forgeability. As described above, one solution is to increase aluminum content, to 0.05 to 0.15 weight percent, for example, to provide sufficient deoxidation and inhibit breakage during forging. Other strategies for providing a sufficient level of deoxidation to ensure suitable hot workability in modified MP35N alloy including reduced levels of titanium are discussed in Example 3 below.

EXAMPLE 2

Processing and Testing Procedures

For comparison purposes, alloys were produced with a standard MP35N alloy chemistry and with a modified MP35N chemistry including reduced levels of titanium. The experimental modified alloy chemistry is provided in Table 5 and included a significantly reduced level of titanium relative to the typical chemistry of conventional MP35N alloy (about 0.95 weight percent).

TABLE 5

| Element | Content (weight percent) |
|---|---|
| Carbon | 0.006 |
| Manganese | 0.01 |
| Silicon | 0.01 |
| Phosphorus | Less than 0.003 |
| Sulfur | 0.0006 |
| Chromium | 20.06 |
| Nickel | 36.75 |
| Molybdenum | 10.32 |
| Iron | 0.12 |
| Titanium | 0.01 |
| Boron | 0.008 |
| Cobalt | Balance |

The alloys were provided as 3,000 lb. VIM electrodes, which were VAR remelted into 17-inch diameter ingots. Each VAR ingot was homogenized to reduce microsegregation, and then rotary forged on a GFM machine to produce a 4-inch thick billet. Each billet was hot rolled on a continuous rolling mill to 0.219-inch thick coil. The coil was annealed, shaved to 0.216 inch thick and pickled in preparation for drawing. Drawing was conducted using carbide dies and powder lubricants to 0.064 inch. Additional processing to a final diameter of 0.007 inch was performed using diamond dies and mineral oil lubricants. For evaluation of the materials, the final wire diameter was to be 0.007 inch, with an allowable variation of +/−0.0002 inch, and a goal was to maintain an ultimate tensile strength of 300-320 ksi in the final wire.

A description of test procedures used to evaluate the alloys and wire drawn from the alloys, and several observations derived from the testing follow.
Microcleanliness A series eight ASTM F 562 standard samples were cut from 0.100-inch diameter wire hard drawn from MP35N alloy. The eight samples represented five separate melted master heats of conventional MP35N alloy. Two samples of a modified reduced-titanium MP35N alloy also were cut from 1.0-inch and 0.216-inch diameter hard drawn material produced from the same melted master heat. All samples were mounted in a thermosetting compound to provide a longitudinal section through the entire length of each segment. The mounted specimens were ground and polished metallographically to obtain a polished plane near the longitudinal center of the samples.

The prepared sections were examined in a scanning electron microscope (SEM) using backscattered electron imaging (BEI). For each sample section, 160 images showing a representative area of the prepared section were acquired at a magnification of 1000× for a total examined area of 1.77 mm$^2$. Analysis of features appearing darker or brighter than the background was conducted using image analysis software. Contrast was adjusted so that features having a higher mean atomic number than the matrix would appear brighter compared with those features having a lower mean atomic number. The largest dimension was recorded for each individual feature in each of the images. The imaged inclusions were categorized by largest dimension into 1 micrometer groups up to the largest inclusion detected. It was believed that some largest dimension measurements could be the result of discrete inclusions occurring in a "stringer" formation, but not discernable as an individual inclusion. Features smaller than 0.2 micrometer were not counted.

The foregoing analysis was performed on each of the 160 images of each sample section. In this way, a direct comparison of cleanliness between the standard MP35N alloy and the experimental low-titanium alloy was accomplished. Selected inclusions were examined at higher magnifications, and qualitative chemical analysis was performed on several of the inclusions by energy dispersive X-ray spectroscopy (EDS).
Grain Size Grain size analysis was performed against samples of the conventional MP35M alloy to confirm that grain size of the modified MP35N alloy is similar. Grain size was determined using the Abrams three circle intercept procedure described n ASTM testing specification E112. Samples were taken at the process anneal size (0.010 inch) for the 0.007-inch finished wire.
Surface Analysis In order to visually inspect the materials, three fifteen-foot samples of 0.007-inch wire were obtained from each heat of the conventionalMP35N alloy and from the modified MP35N alloy. Each sample was visually rated at a magnification of 30× in three datasets at the beginning, middle, and end of the sample. Each dataset consisted of four adjacent one-foot sections. Each section was rated to the following criteria: 1=accept, 2=marginal acceptance, 3=marginal reject, 4=reject, and 5=gross reject. The assigned level of acceptability was based on current demand in the cardiovascular market for surface integrity on implantable wire products.

Fourteen sections of the conventional MP35N alloy 0.007-inch wire and sixteen sections of 0.007-inch wire produced from the modified MP35N alloy also were evaluated for surface defects using eddy current sensors. A detection threshold was set that would intercept a frequency of naturally occurring eddy current signals with a skewed right distribution in intensity. This distribution is typical of naturally occurring surface and exposed subsurface features on a wire. The number of over-threshold signals per 1000-foot section was counted in order to characterize the typical surface variation of each sample.
Mechanical Properties Tensile properties were measured according to the most recent revision of ASTM E8, "Standard Test Methods for Tension Testing Metallic Materials". To evaluate fatigue properties, wire samples were subjected to accelerated fatigue testing using rotary beam cycle testing equipment. Results from this type of accelerated fatigue testing have historically shown good correlation to coil flex life testing. As is generally known in the art, rotary beam testing involves placing a sample under cyclic tensile and compressive stresses. During each rotation, a portion of the specimen in tension is placed in compression and is then cycled back into tension. In this way, stresses are completely reversed in a cyclic manner. The high cycle rate of 3600 rpm used in the testing has been shown to produce repeatable results.

To obtain a desired stress level during testing, a cut length of material was positioned around a specified radius. Seven samples of each heat of the conventional MP35N alloy and the modified alloy were tested at various stress levels. Failure was considered to occur if a wire sample broke. The testing equipment sensed wire breakage and recorded test length to breakage in minutes.

Experimental Results

Microcleanliness

A comparison of cleanliness between the conventional MP35N material and the modified reduced-titanium MP35N material was accomplished by evaluating the frequency distribution of inclusion size in the 1 micrometer groups for the median size inclusion and the $99^{th}$ percentile inclusion limit. The largest inclusion size and the total number of inclusions found for each sample were evaluated for the mean and standard deviation of each material type. Table 6 summarizes data for each material type.

TABLE 6

| Material | Median Size Inclusion (um) | $99^{th}$ Percentile Incl. Limit (um) | Total Inclusions Found - Median | Total Inclusions Found - Std. Dev. | Largest Inclusion Found - Mean (um) | Largest Inclusion Found - Std. Dev. (um) |
|---|---|---|---|---|---|---|
| Standard MP35N | 0.5 | 6.34 | 1623 | 435 | 31.98 | 18.83 |
| Modified MP35N Alloy | 0.5 | 3.43 | 668 | 279 | 4.20 | 0.71 |

Figure 6:
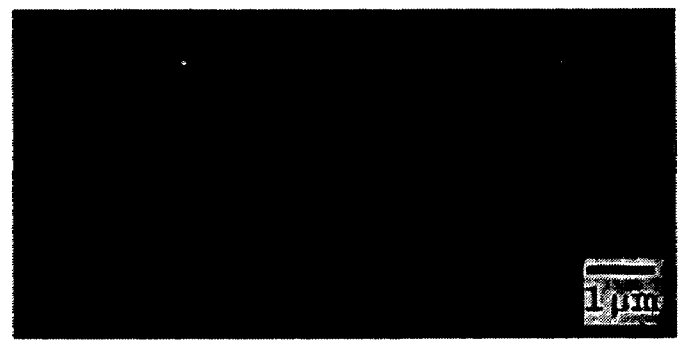
FIG. 6 is an SEM image, formed using BEI, of an inclusion of typical size in a low-titanium, low-nitrogen experimental MP35N material considered in Example 2 herein.
Figure 7:
FIG. 7 an SEM image, formed using BEI, of the largest inclusion found in a low-titanium, low-nitrogen experimental MP35N material considered in Example 2 herein.
Figure 8:
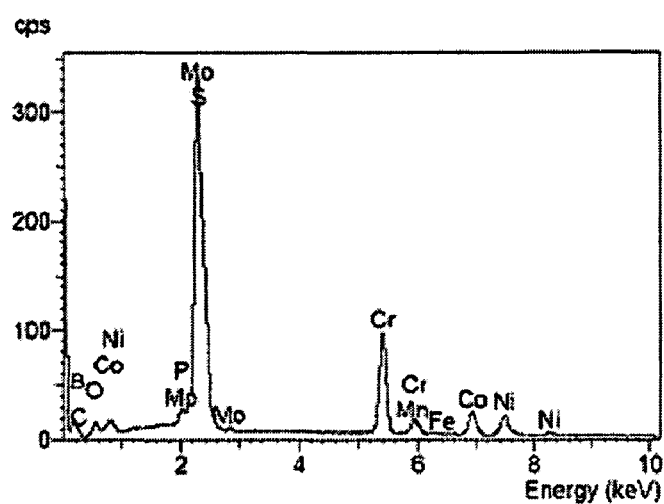
FIG. 8 is a typical EDS spectrum for dark inclusions in a low-titanium, low-nitrogen experimental MP35N material considered in Example 2 herein.

All samples contained features that appeared brighter or darker than the bulk material using BEI. Darker features had a generally rounded morphology and were typically randomly scattered throughout the samples. The majority of the darker features were inclusions with high concentrations of magnesium and oxide. Some inclusions also contained sulfur. FIG. 6 is an image of an inclusion of typical size in the modified alloy, while FIG. 7 is an image of the largest inclusion found in the experimental modified MP35N alloy. FIG. 8 is a typical EDS spectra for the dark inclusions in the experimental alloy.

Figure 9:
FIG. 9 is an SEM image, formed using BEI, of a brighter than background inclusion found in a low-titanium, low-nitrogen experimental MP35N material considered in Example 2 herein.
Figure 10:
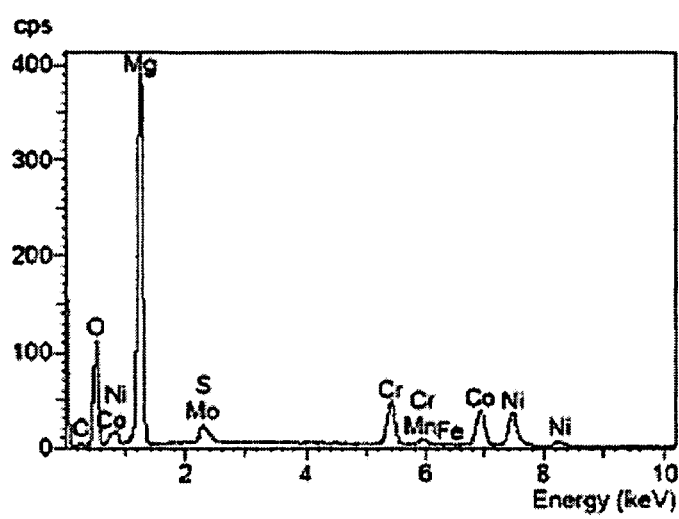
FIG. 10 is a typical EDS spectrum for bright inclusions in a low-titanium, low-nitrogen experimental MP35N material considered in Example 2 herein.

FIG. 9 is an example of features brighter than the background found in the modified MP35N alloy. These features were of a generally rounded morphology and existed randomly and in stringers. Many of the largest features were adjoining bright inclusions. A typical EDS spectrum for the bright inclusions in the low-titanium alloy is shown in FIG. 10. Due to the small size of the inclusions, the analysis is a composite of the inclusions and the surrounding base metal.

Figure 11:
FIG. 11 is an SEM image, formed using BEI, of a typical over medium size inclusion in a conventional MP35N material considered in Example 2 herein.
Figure 12:
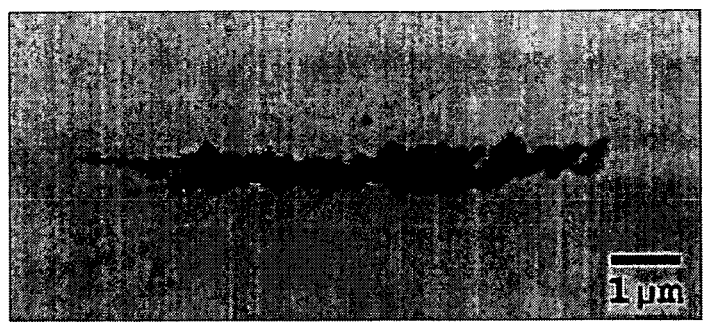
FIG. 12 is an SEM image, formed using BEI, of the largest dark inclusion found in a conventional MP35N material considered in Example 2 herein.

In the samples of wire produced from the conventional MP35N alloy, the largest features were stringers of multiple or broken-up inclusions. The inclusions with the greatest frequency were typically sub-micron inclusions that were randomly scattered throughout the field. The majority of darker features were inclusions with high concentrations of titanium and nitrogen. Some of the darker features consisted of a center that was high in magnesium, aluminum, and oxygen with an outer region containing titanium and nitrogen. Other darker features were inclusions with high concentrations of magnesium and/or aluminum, along with oxygen. FIGS. 11 and 12 are micrographs of typical over median size inclusions present in the conventional MP35N alloy. It is noted that FIGS. 11 and 12 depict images taken at 10 to 20 times less magnification than the images in FIGS. 6 and 7, and, therefore, the inclusions shown in FIGS. 11 and 12 are substantially larger in size.

Figure 13:
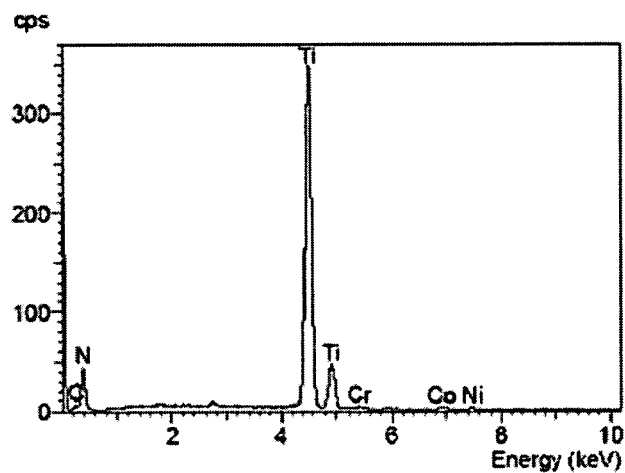
FIG. 13 is a typical EDS spectrum of darker than background inclusions found in a conventional MP35N material considered in Example 2 herein.
Figure 14:
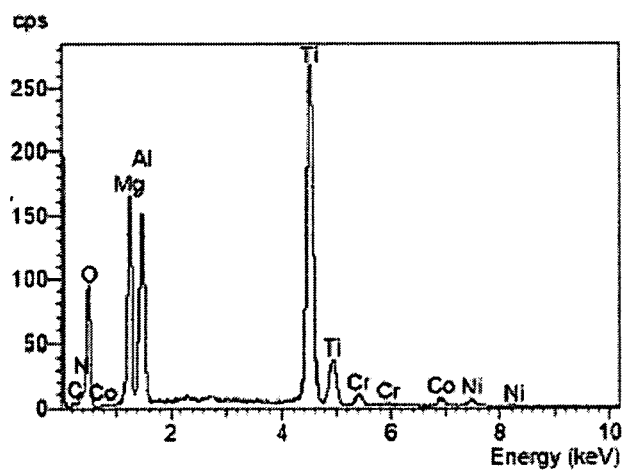
FIG. 14 is a typical EDS spectrum of a darker center region of an inclusion in a wire of a conventional MP35N material considered in Example 2 herein.

FIGS. 13 and 14 show typical EDS spectra of dark inclusions found in the conventional MP35N alloy. FIG. 13 depicts an overall spectrum of an inclusion, while FIG. 14 depicts a spectrum of the darker center region of a dark inclusion in the material.

Figure 15:
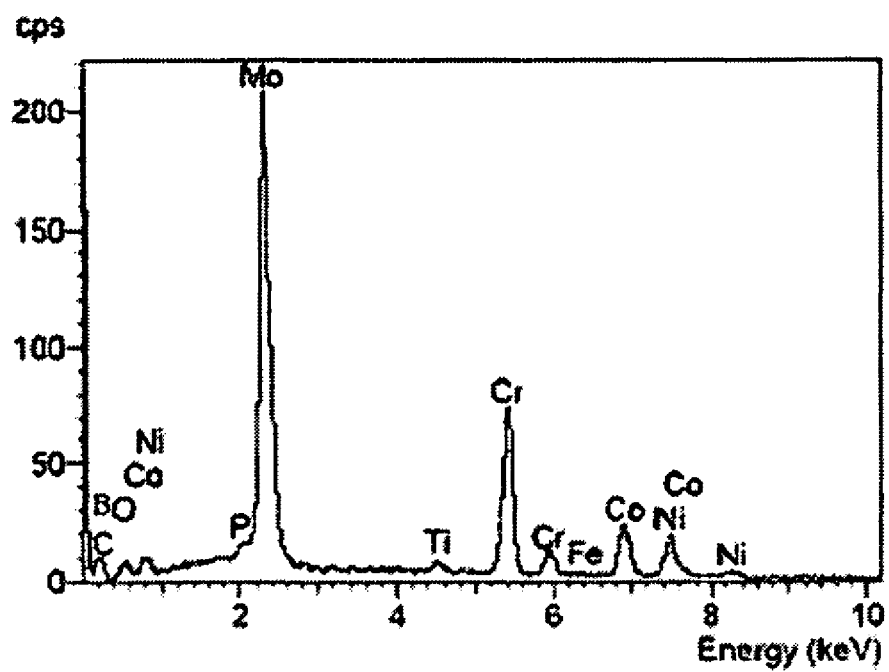
FIG. 15 is an EDS spectrum of a typical bright inclusion in a wire of a conventional MP35N material considered in Example 2 herein.

The features brighter than the background in wire samples made from the conventional MP35N alloy were generally rounded. The features were in stringers and randomly scattered. Some clusters of bright features were also observed. Many of the largest features were adjoining bright inclusions. EDS analysis of the bright features indicated high concentrations of molybdenum and boron. An EDS spectrum of a typical bright inclusion is shown in FIG. 15. Due to the generally small size of such bright inclusions, the analysis underlying FIG. 15 is a composite of the inclusions and the surrounding base metal.

Grain Size

Figure 16:
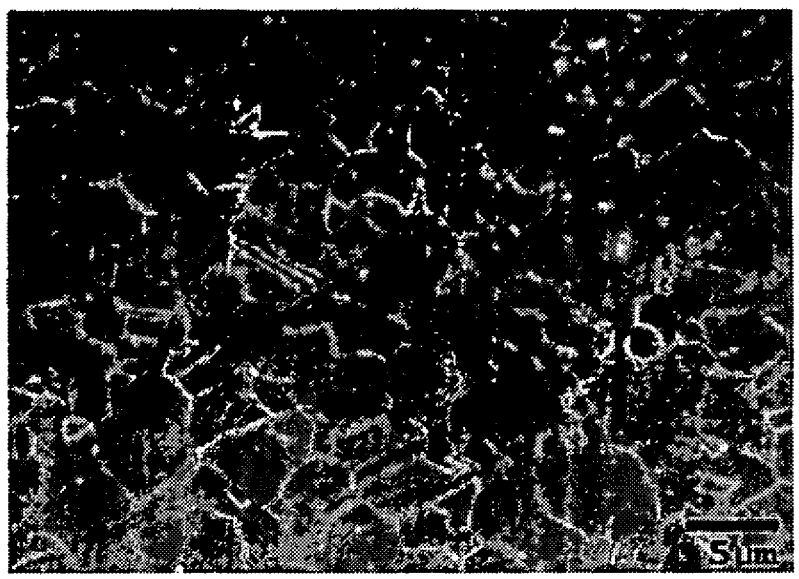
FIGS. 16 and 17, respectively, are photomicrographs of prepared longitudinal and transverse sections of a conventional MP35N material considered in Example 2 herein.
Figure 17:
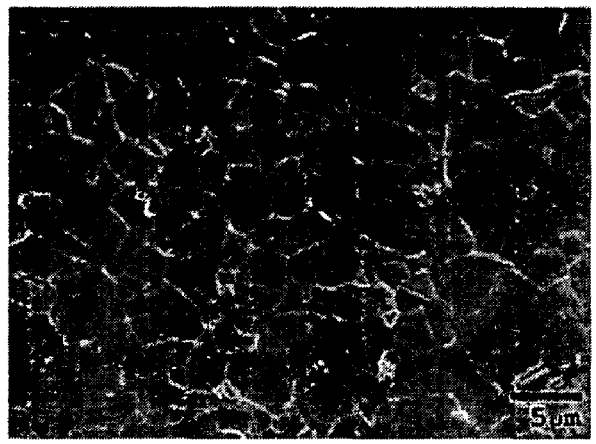
Figure 18:
FIGS. 18 and 19, respectively, are photomicrographs of prepared longitudinal and transverse sections of a low-titanium, low-nitrogen experimental MP35N material considered in Example 2 herein.
Figure 19:
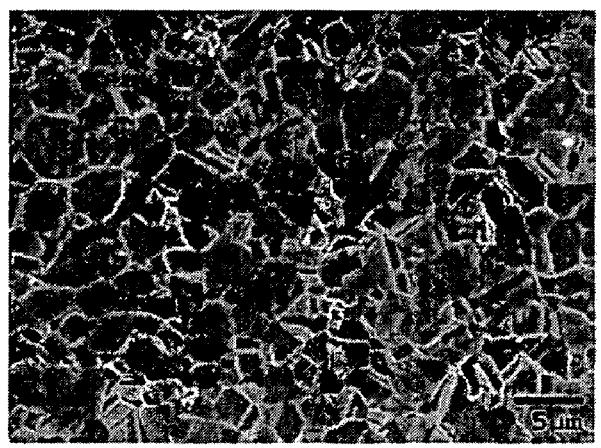

Results indicate that the experimental modified MP35N alloy maintains desirable grain size properties that are similar to conventional MP35N alloy meeting ASTM specification F 562. Table 7 summarizes the grain size results. FIGS. 16 through 18 are photomicrographs showing sample grain sizes. FIGS. 16 and 17 are longitudinal and transverse sections, respectively, of the conventional MP35N material that was evaluated. FIGS. 18 and 19 are longitudinal and transverse sections, respectively, of the experimental modified MP35N alloy.

TABLE 7

| Grain Size | Conventional MP35N Alloy (meets ASTM F 562) | Modified (Reduced Ti) MP35N Alloy |
|---|---|---|
| Longitudinal | 14.6 | 14.3 |
| Transverse | 14.5 | 14.4 |

Surface Analysis

With respect to the visual rating analysis, interpretation of the average visual per foot data indicated a 46% improvement in surface performance of the experimental MP35N material as compared to the conventional MP35N material. Inter-pretation of the average standard deviation in rating between one-foot sections indicated a 54% improvement in surface consistency of the experimental material as compared to the conventional MP35N material. The range for over threshold signals between 1000-foot sections indicated a 65% improvement in surface consistency of the experimental material as compared to the conventional MP35N material.

With respect to eddy current analysis, interpretation of the average over threshold signals per 1000-foot data indicated a 69% improvement in surface and subsurface performance of the experimental modified MP35N alloy as compared to the evaluated conventional MP35N alloy. Interpretation of the average range for over threshold signals between 1000-foot sections indicated a 65% improvement in surface consistency of the experimental alloy as compared to the conventional MP35N alloy that was evaluated.

Mechanical Properties

As shown in Table 8, tensile properties of the experimental modified MP35N material were comparable with the sample of conventional MP35N material. The test results were obtained using a 200 lb. load cell, 10-inch gauge length, 5-inch/min. cross head speed on an Instron testing apparatus.

TABLE 8

|  | Conventional MP35N Alloy (meets ASTM F 562) | Modified (Reduced Ti) MP35N Alloy |
| --- | --- | --- |
| Diameter (inch) | 0.00695 | 0.00695 |
| Ultimate Tensile Strength (psi) | 307,618 | 313,153 |
| Yield Strength | 287,584 | 284,685 |
| Elong. | 2.9% | 3.1% |

Fatigue testing was performed on monofilament wire produced from the experimental and standard alloys using a Valley Instruments Rotary Beam Tester, Model 10040, which has a single drive chuck. Testing was performed in air at 65-75° F. A "runout" (i.e, an infinite number of cycles) was considered to be 54 million cycles (about 15,000 minutes) without wire breakage. Test results on the average number of cycles completed for the sample types at several stress value levels are presented in Table 9.

TABLE 9

| Stress Value | Standard MP35N Alloy (ASTM F 562) (cycles) | Modified MP35N Alloy (cycles) |
| --- | --- | --- |
| 250 ksi | 11,129 | 9,586 |
| 200 ksi | 27,067 | 33,778 |
| 150 ksi | 86,534 | 144,926 |
| 125 ksi | 218,654 | 9,834,578 |
| 110 ksi | 1,154,093 | 33,471,607 |
| 100 ksi | 6,774,228 | 54,000,000 |
| 90 ksi | 17,608,305 | Not tested[1] |

Figure 20:
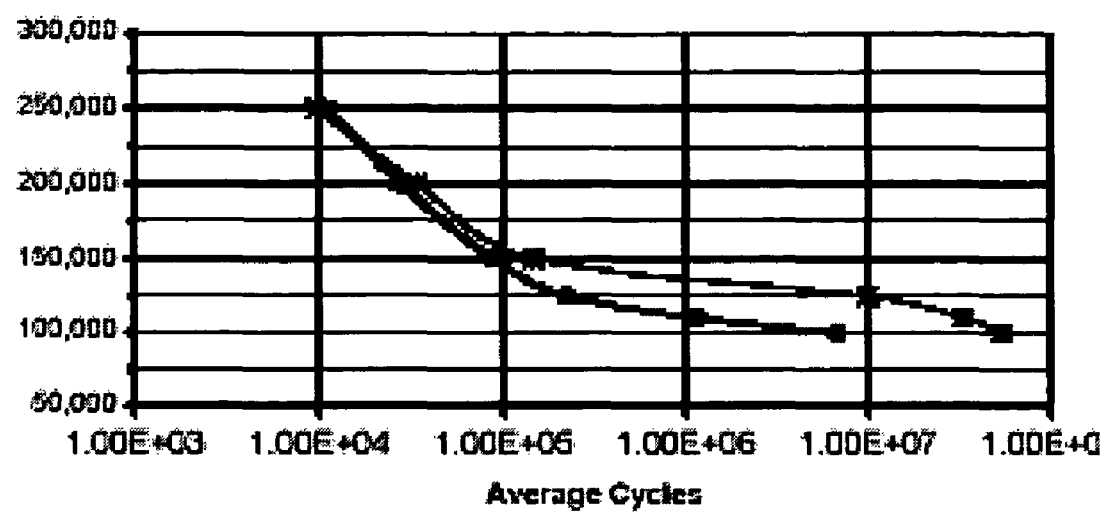
FIG. 20 is an S-N plot of average number of stress cycles to failure versus stress level for a conventional MP35N material and a low-titanium, low-nitrogen experimental MP35N material considered in Example 2.

Beginning with a relatively high stress level of 200 Ksi, the improvement achieved by the experimental low-titanium alloy is evident. The improvement continues and is most dramatic nearer the 100 ksi stress level, which is considered to represent the actual in-use range for surgical implants such as pacing leads. FIG. 20 presents the data from Table 9 arranged in the typical S-N curve format.

An objective of fatigue testing is to establish the endurance limit of a material. The endurance limit of an alloy is the limiting stress below which the metal will theoretically withstand an infinite number of cycles without fracture. As shown in Table 9 and FIG. 20, the endurance limit of the conventional MP35N alloy is less than 90 ksi in the testing conducted. The experimental modified MP35N alloy, however, withstood a runout at 100 ksi. This suggests that the endurance limit of the modified material is somewhere between 100 and 110 ksi, while that of the standard MP35N material is significantly less. The fatigue testing indicated that the experimental modified alloy had an endurance limit that is at least 10,000 psi greater than the standard MP35N material. The test results also suggest that the modified chemistry of the experimental material provided an improvement of at least 797% (54,000,000 cycles versus 6,774,228 cycles) at a 100 ksi stress level.

The greater service life for surgical implants suggested by the significantly higher endurance limit of the modified MP35N alloys described herein offers an additional safety margin and confidence level for the medical device design engineer. For example, two major factors contributing to the stress applied to the wire in a pacing coil are the coil diameter and the wire diameter. The higher endurance limit of the modified material may allow the use of smaller diameter coils and/or smaller diameter wire, while providing the same safety margin.

EXAMPLE 3

In light of the failure of heat WE48 in Example 1 above during hot working, the effects of various deoxidation practices on hot workability of modified MP35N alloys within the present disclosure were evaluated. Melt processing was modified in various ways to minimize the level of oxygen in the in the processed material. This was attained by modifying the deoxidation practice employed during VIM melting.

It was determined that late-late additions of nickel calcium, nickel magnesium, or cerium are effective when added during VIM melting to significantly reduce oxygen in the experimental modified MP35F alloys of the present disclosure. Heats WF64, WF65 and WF66 were prepared having the ladle chemistries shown in Table 10. Heat WF64 included a VIM addition of nickel magnesium to provide about 156 ppm magnesium in the alloy. Heat WF 65 included a VIM addition of nickel calcium to provide about 141 ppm calcium in the alloy. Heat WF66 include VIM addition of cerium to provide about 0.01 weight percent cerium on the alloy. Each of these additions was intended to produce oxides and thereby remove oxygen from the alloy that otherwise may contribute to oxygen embrittlement at grain boundaries and promote fracturing during hot working.

The tables included in FIG. 21 characterize the inclusions found using SEM to analyze as-rolled 1.5-inch RD micros of the alloys of heats WF64, WF65 and WF66. As shown in FIG. 21, the inclusions found in the alloys were almost exclusively oxides of the particular deoxidizing species used (calcium oxide, magnesium oxide, or cerium oxide). No appreciable level of TiN or mixed metal carbonitride particles was found in the microstructures of the alloys produced from the three heats. The alloys produced from these heats were found to be readily hot workable. Thus, it was determined that the processing of modified MP35N alloy of the present disclosure including low levels of titanium may be modified by VIM addition to provide acceptable hot workability without promoting formation of TiN or mixed metal carbonitride particles.

TABLE 10

| Element | Heat WF64 | Heat WF65 | Heat WF66 |
| --- | --- | --- | --- |
| Ni | 36.33 | 36.30 | 36.10 |
| Co | 33.48 | 33.52 | 33.66 |
| Cr | 20.02 | 20.00 | 20.04 |
| Mo | 10.04 | 10.02 | 10.07 |
| Fe | 0.03 | 0.03 | 0.03 |
| Al | 0.01 | 0.04 | 0.01 |
| Ti | 0.01 | 0.01 | 0.01 |
| V | 0.01 | 0.01 | 0.01 |
| Zr | 0.01 | 0.01 | 0.01 |
| Nb | 0.01 | 0.01 | 0.01 |
| W | 0.01 | 0.01 | 0.01 |
| Ta | 0.01 | 0.01 | 0.01 |
| Si | 0.01 | 0.01 | 0.01 |
| Mn | 0.01 | 0.01 | 0.01 |
| Cu | 0.01 | 0.01 | 0.01 |
| P | 0.005 | 0.005 | 0.005 |
| S | less than 0.0003 | less than 0.0003 | less than 0.0003 |

TABLE 10-continued

| Element | Heat WF64 | Heat WF65 | Heat WF66 |
|---|---|---|---|
| C | 0.001 | 0.002 | 0.002 |
| B | 0.005 | 0.004 | 0.007 |
| N | 0.0007 | 0.0009 | 0.0008 |
| O | 0.0018 | 0.0038 | 0.0019 |
| Ca | less than 10 | 141 | less than 10 |
| Mg | 156 | 4 | 6 |
| Ce | 0 | 0 | 0.01 |

Based on the results observed in connection with Example 3 and with respect to the deoxidizing aluminum used addition in connection with Example 1, a VIM addition of suitable materials to provide the alloy with one or more of 0.05 to 0.15 weight percent aluminum, 5 to 20 ppm calcium, 5 to 50 ppm magnesium, and 5 to 50 ppm cerium may be desirable to provide the modified MP35N alloys of the present disclosure with suitable hot workability.

It will be understood that the present description illustrates those aspects of the invention relevant to a clear understanding of the invention. Certain aspects of the invention that would be apparent to those of ordinary skill in the art and that, therefore, would not facilitate a better understanding of the invention have not been presented in order to simplify the present description. Although embodiments of the present invention have been described, one of ordinary skill in the art will, upon considering the foregoing description, recognize that many modifications and variations of the invention may be employed. All such variations and modifications of the invention are intended to be covered by the foregoing description and the following claims.

What is claimed is:

1. An alloy having favorable fatigue resistance and comprising:
   at least 20 weight percent cobalt;
   32.7 to 37.3 weight percent nickel;
   18.75 to 21.25 weight percent chromium;
   8.85 to 10.65 weight percent molybdenum;
   less than 30 ppm nitrogen;
   less than 0.7 weight percent titanium;
   at least one of at least 0.05 to 0.15 weight percent aluminum, at least 5 to 20 ppm calcium, at least 5 to 50 ppm magnesium, and at least 5 to 50 ppm cerium; and
   no greater than 1.05 weight percent iron;
   no greater than 0.035 weight percent carbon; and
   wherein the alloy includes generally spherical oxide inclusions and is substantially free of titanium nitride and mixed metal carbonitride inclusions.

2. The alloy of claim 1, comprising less than 20 ppm nitrogen.

3. The alloy of claim 1, further comprising less than 0.03 weight percent titanium.

4. The alloy of claim 1, further comprising:
   no greater than 0.18 weight percent manganese;
   no greater than 0.17 weight percent silicon;
   no greater than 0.020 weight percent phosphorus;
   no greater than 0.015 weight percent sulfur; and
   no greater than 0.020 weight percent boron.

5. The alloy of claim 1, comprising:
   33.0 to 37.0 weight percent nickel;
   19.0 to 21.0 weight percent chromium; and
   9.0 to 10.5 weight percent molybdenum.

6. The alloy of claim 5, further comprising:
   no greater than 0.025 weight percent carbon;
   no greater than 0.15 weight percent manganese;
   no greater than 0.15 weight percent silicon;
   no greater than 0.015 weight percent phosphorus;
   no greater than 0.010 weight percent sulfur;
   no greater than 1.0 weight percent iron; and
   no greater than 0.015 weight percent boron.

7. The alloy of claim 6, comprising less than 20 ppm nitrogen.

8. The alloy of claim 6, further comprising less than 0.03 weight percent titanium.

9. The alloy of claim 1, comprising 0.05 to 0.15 weight percent aluminum.

10. The alloy of claim 1, comprising 5 to 20 ppm calcium.

11. The alloy of claim 1, comprising 5 to 50 ppm calcium.

12. The alloy of claim 1, comprising 5 to 50 ppm cerium.

13. The alloy of claim 1, wherein the alloy does not exhibit significant oxygen embrittlement at grain boundaries.

14. The alloy of claim 1, wherein the alloy is substantially free of titanium.

15. The alloy of claim 1, wherein the alloy is substantially free of nitrogen.

16. The alloy of claim 1, wherein the alloy has an endurance limit greater than 100 ksi.

17. The alloy of claim 1, wherein the alloy qualifies for use in surgical implant applications under ASTM standard specification F 562.

18. An article of manufacture comprising the alloy of any of claims 1, 2, 3-7, 8, and 9-17.

19. The article of manufacture of claim 18, wherein the article of manufacture is selected from a bar, a wire, a tube, a surgical implant device, a component for a surgical implant device, an implantable defibrillator, a component for an implantable defibrillator, an implantable pacemaker, a component for an implantable pacemaker, a pacing lead, and a cardiac stent.

20. The article of manufacture of claim 18, wherein the article of manufacture is one of a bar and a wire, and qualifies for use in surgical implant applications under ASTM standard specification F 562.

21. The alloy of claim 1, consisting of:
   at least 20 weight percent cobalt;
   32.7 to 37.3 weight percent nickel;
   18.75 to 21.25 weight percent chromium;
   8.85 to 10.65 weight percent molybdenum;
   less than 30 ppm nitrogen;
   less than 0.7 weight percent titanium;
   at least one of at least 0.05 to 0.15 weight percent aluminum, at least 5 to 20 ppm calcium, at least 5 to 50 ppm magnesium, and at least 5 to 50 ppm cerium;
   no greater than 1.05 weight percent iron;
   no greater than 0.035 weight percent carbon;
   no greater than 0.18 weight percent manganese;
   no greater than 0.17 weight percent silicon;
   no greater than 0.020 weight percent phosphorus;
   no greater than 0.015 weight percent sulfur;
   no greater than 0.020 weight percent boron; and
   incidental impurities,
   wherein the alloy includes generally spherical oxide inclusions and is substantially free of titanium nitride and mixed metal carbonitride inclusions.

22. The article of manufacture of claim 18, wherein the article of manufacture is a wire.

* * * * *

UNITED STATES PATENT AND TRADEMARK OFFICE
CERTIFICATE OF CORRECTION

| | | |
|---|---|---|
| PATENT NO. | : 8,048,369 B2 | Page 1 of 1 |
| APPLICATION NO. | : 10/656918 | |
| DATED | : November 1, 2011 | |
| INVENTOR(S) | : Forbes-Jones et al. | |

It is certified that error appears in the above-identified patent and that said Letters Patent is hereby corrected as shown below:

On the Title Page, Item (73), Assignee: delete "ATI Properties, Inc., Albany, OR (US)" and substitute -- ATI Properties, Inc., Albany, OR (US); Fort Wayne Metals Research Products Corp., Fort Wayne, IN (US) -- therefor Signed and Sealed this
Twenty-fourth Day of July, 2012

David J. Kappos
*Director of the United States Patent and Trademark Office*